United States Patent [19]

Odake et al.

[11] Patent Number: 5,100,874
[45] Date of Patent: Mar. 31, 1992

[54] HYDROXAMIC ACID TETRAPEPTIDE DERIVATIVES

[75] Inventors: Shinjiro Odake, Takaoka; Toru Okayama, Ishikawa; Masami Obata; Tadanori Morikawa, both of Toyama; Yutaka Nagai, Koshigaya, all of Japan

[73] Assignee: Fuji Yakuhin Kogyo Kabushiki Kaisha, Toyama, Japan

[21] Appl. No.: 392,931

[22] PCT Filed: Dec. 16, 1988

[86] PCT No.: PCT/JP88/01281
  § 371 Date: Aug. 4, 1989
  § 102(e) Date: Aug. 4, 1989

[87] PCT Pub. No.: WO89/05819
  PCT Pub. Date: Jun. 29, 1989

[30] Foreign Application Priority Data

Dec. 17, 1987 [JP] Japan .................. 62-317364

[51] Int. Cl.$^5$ .......................... A61K 7/02; C07K 5/10
[52] U.S. Cl. .................................... 514/18; 530/330
[58] Field of Search ..................... 514/18; 530/330

[56] References Cited

U.S. PATENT DOCUMENTS

| | | |
|---|---|---|
| 4,568,666 | 2/1986 | McCullagh et al. . |
| 4,595,700 | 6/1986 | Donald et al. . |
| 4,599,361 | 7/1986 | Dickens et al. . |
| 4,681,966 | 7/1987 | Donald et al. . |
| 4,687,841 | 8/1987 | Spilburg et al. . |
| 4,720,486 | 1/1988 | Spilburg et al. . |
| 4,743,587 | 5/1988 | Dickens et al. . |

FOREIGN PATENT DOCUMENTS

| | | |
|---|---|---|
| 61-103896 | 5/1986 | Japan . |
| 61-152650 | 7/1986 | Japan . |
| 62-103052 | 5/1987 | Japan . |

*Primary Examiner*—Lester L. Lee
*Attorney, Agent, or Firm*—Birch, Stewart, Kolasch & Birch

[57] ABSTRACT

New peptide derivatives of which utility in the treatment of such diseases as rheumatoid arthritis, peridental diseases, corneal ulcer and epidermolysis bullosa is expected. These compounds are hydroxamic acid derivatives of tetrapeptides having a specific inhibitory activity against collagenase derived from vertebrates.

10 Claims, No Drawings

HYDROXAMIC ACID TETRAPEPTIDE DERIVATIVES

FIELD OF THE INVENTION

The present invention relates to new peptidylhydroxamic acid derivatives which specifically inhibit the action of collagenase of vertebrate origin, as well as to collagenase inhibitors containing these new peptidylhydroxamic acid derivatives as active ingredient.

1. Background Art

Collagenase is an enzyme which decomposes collagen, one of the main protein components constituting connective tissues.

Animals in pathological conditions show an abnormal overaction of collagenase in processes of the destruction and repair of tissues. Such abnormal overaction of collagenase is observed, for example, in such cases as rheumatoid arthritis, peridental diseases, corneal ulcer and epidermolysis bullosa, where inhibition of the action of collagenase provides a useful means for treating such diseases.

2. Prior Art

Some peptidylhydroxamic acids have heretofore been known as substances which exhibit inhibitory action on collagenase. Thus, William M. Moore et al. reported benzyloxycarbonyl-prolyl-leucyl-glycylhydroxamic acid (Z-Pro-Leu-Gly-NHOH) (see William M. Moore and Curtis A. Spilburg, Biochemical and Biophysical Research Communications, Vol. 136, No. 1, Pages 390–395, 1986). Furthermore as other peptide-based synthetic collagenase inhibitors were reported mercapto-containing compounds (see Robert D. Gray, Hossain H. Saneii and Arno F. Spatola, Biochemical and Biophysical Research Communications, Vol. 101, No. 4, Pages 1251–1258, 1981; Charles F. Vencill, David Rasnick, Katherine V. Crumley, Norikazu Nishino and James C. Powers, Biochemistry 24, 3149–3157, 1985) or carboxyl group-containing compounds (see Jean-Marie Delaisse, Yves Eeckhout, Christopher Sear, Alan Galloway, Keith McCullagh and Gilbert Vaes, Biochemical and Biophysical Research Communications, Vol. 133, No. 2, Pages 483–490, 1985).

The purpose of the present invention is to provide new peptide compounds which selectively inhibit the action of collagenase derived from vertebrates without inhibiting other protease actions (i.e. which exhibit an inhibitory action of high specificity), and which have low toxicity, improved metabolic rate and other improved properties.

The present inventors, as a result of extensive researches aiming at developing new peptide compounds with such preferable properties have achieved the present invention, according to which it has been found that new peptidylhydroxamic acid derivatives of the general formula (I):

$$X^1\text{-}X^2\text{-}X^3\text{-}X^4\text{-NHOH} \quad (I)$$

wherein each of $X^1$, $X^2$, $X^3$ and $X^4$ is an α-amino acid residue; the carboxyl group of α-amino acid $X^1$ forms a peptide bond together with the amino group of α-amino acid $X^2$; the carboxyl group of α-amino acid $X^2$ forms a peptide bond together with the amino group of α-amino acid $X^3$; the carboxyl group of α-amino acid $X^3$ forms a peptide bond together with the amino group of α-amino acid $X^4$ and the carboxyl group of α-amino acid $X^4$ forms an amido bond together with —NHOH; and the hydrogen atom of the amino group in α-amino acid $X^1$ may be replaced by an aliphatic or aromatic carbyloxycarbonyl or acyl group which itself may have substituents, as well as their salts, are suitable for the purpose mentioned above.

The present inventors have succeeded in providing new compounds of the general formula (I) suitable for the purpose mentioned above by using, as an index, inhibitory action on each of the seven enzymes, i.e. collagenase from human fibroblasts, collagenase from tadpoles, collagenase from bacteria, urease, thermolysin, α-chymotrypsin and trypsin to screen compounds for strong inhibitory action on the first two enzymes.

The preparation of new peptidylhydroxamic acid derivatives of the general formula (I) are carried out by processes which can be divided roughly into (A) and (B) below:

(A) Process where a compound of the formula Boc-$X^4$-NHOBzl is used as starting material; the peptide chain is extended on the Boc-N group side first to form the group $X^3\text{-}X^4\text{-}$, which is converted, via the group $X^2\text{-}X^3\text{-}X^4\text{-}$ into the group $X^1\text{-}X^2\text{-}X^3\text{-}X^4\text{-}$; and finally the O-benzyl on the hydroxamic acid side is eliminated to give the desired compound; and (B) Process where a compound of the formula Boc-$X^4$-$OR^2$ is used as starting material to synthesize the corresponding peptide derivative:

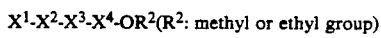
$X^1\text{-}X^2\text{-}X^3\text{-}X^4\text{-}OR^2(R^2$: methyl or ethyl group)

which is then reacted with hydroxylamine to give the desired compound.

In the above mentioned processes, any means conventionally used in the peptide synthetic chemistry may be employed as specific means for condensing amino acids for formation of peptide chains; for protecting with protecting groups the amino, imino, carboxyl and/or hydroxyl groups which may be present in their structure; and for eliminating such protecting groups. Such means is described in detail in the literature for example, in Tanpaku-shitsu Kagaku (Protein chemistry) I, Amino-san (Amino acid)·Peputido (Peptide), ed. by Shiro Akabori, Takeo Kaneko and Kozo Narita, Kyoritsu Shuppan, 1969.

As means for carrying out the condensation mentioned above there may be mentioned a variety of methods, for example, dicyclohexylcarbodiimide (DCC) method, N,N'-dimethylaminopropylethylcarbodiimide (WSCD) method, mixed acid anhydride method, azide method, active ester method, oxidation reduction method and DCC-additive (e.g. 1-hydroxybenzotriazole, N-hydroxysuccinimide and N-hydroxy-5-norbornene-2,3-dicarboxyimide). Where the reaction is carried out using a solvent, there may be used as such solvent N,N-dimethylformamide (DMF), tetrahydrofuran (THF), methylene chloride, dioxane and ethyl acetate or mixtures thereof.

As examples of the protecting groups mentioned above, there may be mentioned benzyloxycarbonyl (Z), t-butyloxycarbonyl (Boc), benzoyl (Bz), acetyl, formyl, p-methoxybenzyloxycarbonyl and trifluoroacetyl for amino or imino group; methyl (OMe), ethyl (OEt), t-butyl, benzyl (OBzl) and p-nitrobenzyl for carboxyl group; and acetyl, benzyl, benzyloxycarbonyl and t-butyl for hydroxyl group. In the foregoing description of compounds or groups, the parenthesized signs are abbreviations standing for such compounds or groups, and these abbreviations are also used as such in the present specification.

As means for eliminating the protecting groups mentioned above, there may be mentioned, for example, catalytic hydrogenation method and methods using trifluoroacetic acid, hydrogen fluoride, hydrogen bromide, hydrogen chloride, sodium hydroxide, potassium hydroxide, etc.

As pharmacologically acceptable salts of compounds of the general formula (I) according to the present invention, there may be mentioned N-addition salts such as hydrochloride, hydrobromide, sulfate, phosphate, formate, acetate, propionate, malonate, succinate, lactate, oxalate and tartarate, and where the amino group is protected, sodium salt, potassium salt, magnesium salt, calcium salt, aluminum salt, piperidine salt, morpholine salt, dimethylamine salt, diethylamine salt, etc.

The new hydroxamic acid derivatives according to the invention have a potent inhibitory action on collagenase derived from vertebrates. In addition these compounds, as well as their metabolites produced in the body, are presumed to have extremely high safety since the components constituting their structure are naturally occurring amino acids of high safety or derivatives thereof.

The following examples are illustrative of the new compounds of the invention as well as of processes for their preparation.

Abbreviations used in the specification including the working examples to represent amino acids and their derivatives or groups present in the structure of these, reagents, etc. are in accordance with signs customarily used in the field of peptide synthetic chemistry (see IUPAC-IUB Commission on Biological Nomenclature), and have the following meanings:

| | | | |
|---|---|---|---|
| Gly: | Glycine | Ala: | Alanine |
| Ile: | Isoleucine | Leu: | Leucine |
| Pro: | Proline | Val: | Valine |
| Sar: | Sarcosine | Phe: | Phenylalanine |
| Nle: | Norleucine | Ser: | Serine |
| Glu: | Glutamic acid | Gln: | Glutamine |
| Lys: | Lysine | Arg: | Arginine |
| Pgl: | Phenylglycine | Hyp: | Hydroxyproline |
| thioPro: | Thioproline | Asp: | Aspartic acid |
| Asn: | Asparagine | Tyr: | Thyrosine |
| Trp: | Tryptophane | DCC: | Dicyclohexylcarbodiimide |
| HOBt: | 1-Hydroxybenzotriazole | | |
| HOSu: | N-Hydroxysuccinimide | | |
| Ac: | Acetyl | Boc: | t-Butyloxycarbonyl |
| Z: | Benzyloxycarbonyl | Bz: | Benzoyl |
| HPA: | 2-(p-Hydroxyphenyl)propionyl | | |
| ABA: | p-Aminobenzoyl | PTH: | o-Phthalyl |
| HBA: | p-Hydroxybenzoyl | Bzl: | Benzyl ether |
| OBzl: | Benzyl ester | OEt: | Ethyl ester |
| OMe: | Methyl ester | TEA: | Triethylamine |
| THF: | Tetrahydrofuran | DMF: | N,N-dimethylformamide |
| DMSO: | Dimethylsulfoxide | | |
| TLC: | Thin layer chromatography on silica gel | | |

Amino acids referred to in the specification, where there can be optical isomers, are in L-form unless otherwise expressly indicated.

EXAMPLE 1 t-Butyloxycarbonyl-glycyl-L-prolyl-L-leucyl-glycyl-hydroxamic acid (Boc-Bly-Pro-Leu-Gly-NHON)

(A) Synthesis of Boc-Gly-NHOBzl

HCl·NH$_2$OBzl (11.2 g; 70.2 mmol) was suspended in DMF (100 ml) and TEA (11.2 ml; 80.0 mmol) was added dropwise under ice-cooling. HOBt (7.43 g; 55.0 mmol) and Boc-Gly-OH (8.76 g; 50.0 mmol) were then added and the mixture was cooled with a coolant at −20° C. DCC (14.5 g; 70.2 mmol) dissolved in CH$_2$Cl$_2$ (70 ml) was added dropwise. After the dropwise addition, the reaction was allowed to proceed for 1 hour at −10° C. and overnight in a refrigerator. Insolubles were filtered off and the solvent was distilled off under reduced pressure. The residue was dissolved in AcOEt and then washed successively with water, 1N-HCl, water, 10% Na$_2$CO$_3$ and water. The solution was dried over anhydrous MgSO$_4$ and the solvent was distilled off under reduced pressure. The residue was purified by chromatography on silica gel (Fuji Davison BW 200, 300 g; eluted with AcOEt: n-Hexane (=1:1) mixed solvent) to give Boc-Gly-NHOBzl (13 g; 93%) as a pale yellow oil.

TLC (developing solvent: ① CHCl$_3$:MeOH=14:1, ② CHCl$_3$:MeOH:AcOH=95:5:3; color developing method: 0.1% ninhydrin spraying followed by heating) gave single spots at R$_f$①=0.75 and R$_f$②=0.63.

(B) Synthesis of HCl·Gly-NHOBzl 4.5N HCl/AcOEt (30 ml) was added under ice cooling to Boc-Gly-NHOBzl (5.0 g; 17.8 mmol) obtained in (A). The mixture was brought back to room temperature and the reaction was carried out for 1 hour. The solvent was distilled off under reduced pressure and the residue was solidified with Et$_2$O to give Hcl·Gly-NHOBzl (3.60 g; 93%) as a hydroscopic colorless powder.

TLC (developing solvent:① CHCl$_3$:MeOH-:AcOH=5:2:1, ② n-BuOH:AcOH:H$_2$O=4:1:1; color developing method: 0.1% ninhydrin spraying followed by heating) gave single spots at R$_f$①=0.45 and R$_f$②=0.44.

(C) Synthesis of Boc-Leu-Gly-NHOBzl

HCl·Gly-NHOBzl (7.15 g; 33.0 mmol) obtained in (B) was dissolved in a mixed solvent of DMF (20 ml) and THF (80 ml) and TEA (4.9 ml; 35.0 mmol) was added dropwise under ice cooling. After the dropwise addition, HOBt (4.19 g; 31.0 mmol) and Boc-Leu-OH (product from azeotropic dehydration of the monohydrate (7.48 g; 30.0 mmol)) were added and the mixture was cooled with a coolant at −20° C. After DCC (8.05 g; 39.0 mmol) dissolved in THF (20 ml) was added dropwise, the reaction was carried out for 1 hour at −10° C. and overnight in a refrigerator. Insolubles were removed by filtration and the solvent was distilled off under reduced pressure. The residue was dissolved in AcOEt and washed successively with water, 1N-HCl, water, 10% Na$_2$CO$_3$ and water. The solution was dried over anhydrous MgSO$_4$ and the solvent was then distilled off under reduced pressure. The residue was purified by chromatography on silica gel (Fuji Davison BW 200, 600 g; eluted with AcOEt: n-hexane (=2:1) mixed solvent) and then recrystallized from AcOEt-n-hexane mixed solvent to give Boc-Leu-Gly-NHOBzl (10.9 g; 93%) as colorless needles.

m.p. 109°–113° C., specific rotation $[\alpha]_D^{28}$ −8.3 (c=1.0, EtOH).

TLC (developing solvent:① $CHCl_3:MeOH=14:1$, ② $CHCl_3:MeOH:AcOH=80:10:5$; color developing method: 0.1% ninhydrin spraying followed by heating) gave single spots at Rf①=0.58 and Rf,crc/2/ =0.79.

(D) Synthesis of Boc-Gly-Pro-OEt

HCl·Pro-OEt (10.8 g; 60.1 mmol) was dissolved in THF (70 ml). After TEA (8.4 ml; 60.0 mmol) was added dropwise under ice cooling, HOBt (7.43 g; 55.0 mmol) and Boc-Gly-OH (8.76 g; 50.0 mmol) were added. The mixture was cooled with a coolant at −20° C. and DCC (13.4 g; 65.0 mmol) dissolved in THF (30 ml) was added dropwise. The reaction was carried out for 1 hour at −10° C. and overnight in a refrigerator. Insolubles were removed by filtration and the solvent was distilled off under reduced pressure. The residue was purified by chromatography on silica gel (Fuji Davison BW 200, 250 g; eluted with AcOEt: n-hexane (=3:2) mixed solvent) and then recrystallized from AcOEt-n-hexane to give Boc-Gly-Pro-OEt (10.5 g; 85%) as colorless plates. m.p. 56.5°–57.0° C., specific rotation $[\alpha]_D^{28}$ −84.9 (c=1.0, EtOH).

TLC (developing solvent:① $CHCl_3:MeOH=14:1$, ② $CHCl_3:MeOH:AcOH=80:10:5$; color developing method: 0.1% ninhydrin spraying followed by heating) gave single spots at Rf①=0.73 and Rf②=0.90.

(E) Synthesis of Boc-Gly-pro-OH

Boc-Gly-Pro-OEt (4.11 g; 15.0 mmol) obtained in (D) was dissolved in MeOH (30 ml). The reaction was carried out for 1 hour after 2N-NaOH (10 ml) was added under ice cooling, and for 4 hours after the mixture was brought back to room temperature. The MeOH was distilled off under reduced pressure and the pH was adjusted to 2 with 1N-HCl The mixture was extracted three times with AcOEt. The extracts were washed with water and dried over anhydrous $MgSO_4$, and the solvent was distilled off under reduced pressure. The residue was recrystallized from an AcOEt-n-hexane mixed solvent to give Boc-Gly-Pro-OH (3.44 g; 93%) as colorless plates. m.p. 140.5°–141° C., specific rotation $[\alpha]_D^{28}$ −75.5 (c=1.0, EtOH).

TLC (developing solvent:① $CHCl_3:MeOH:AcOH=80:10:5$, ② $n-BuOH:AcOH:H_2O=4:1:1$; color developing method: 0.1% ninhydrin spraying followed by heating) gave single spots at Rf①=0.51 and Rf②=0.51.

(F) Synthesis of Boc-Gly-Pro-Leu-Gly-NHOBzl

To Boc-Leu-Gly-NHOBzl (3.93 g; 10.0 mmol) obtained in (C) was added under ice cooling 4.5N-HCl/AcOEt (40 ml). The mixture was brought back to room temperature and the reaction was then carried out for 1.5 hours. The solvent was distilled off under reduced pressure and the residue was dissolved in DMF (20 ml) and then cooled with a coolant at −20° C. After TEA (1.4 ml; 10 mmol) was added dropwise, HOBt (1.35 g; 10.0 mmol) and Boc-Gly-Pro-OH (2.34 g; 9.50 mmol) obtained in (E) were added and DCC (2.68 g; 13.0 mmol) dissolved in THF (10 ml) was added dropwise. The reaction was carried out at −10° C. for 1 hour and overnight in a refrigerator. After insolubles were removed by filtration, the solvent was distilled off under reduced pressure and the residue was dissolved in AcOEt and washed successively with water, 1N-HCl, water, 10% $Na_2CO_3$ and water. The solution was dried over anhydrous $MgSO_4$ and the solvent was distilled off under reduced pressure. The residue was purified by chromatography on silica gel (Fuji Davison BW 200, 250 g; eluted with $CHCl_3:MeOH$ (=20:1) mixed solvent) to give Boc-Gly-Pro-Leu-Gly-NHOBzl (4.7 g; 90%) as a colorless oil.

Specific rotation $[\alpha]_D^{28}$ −68.6 (c=1.0, EtOH).

TLC (developing solvent:① $CHCl_3:MeOH=14:1$, ② $CHCl_3:MeOH:AcOH=80:10:5$; color developing method: 0.1% ninhydrin spraying followed by heating) gave single spots at Rf①=0.37 and Rf②=0.72.

(G) Synthesis of Boc-Gly-Pro-Leu-Gly-NHOH

Boc-Gly-Pro-Leu-Gly-NHOBzl (1.0 g; 1.83 mmol) obtained in (F) was dissolved in MeOH (20 ml) and the solution was subjected to catalytic hydrogenation at room temperature for 1 hour using 10% Pd-C (50% wet) (0.3 g). The catalyst was removed by filtration and the solvent was then distilled off under reduced pressure. The residue was purified by chromatography on silica gel (Fuji Davison BW 200, 15 g; eluted with $CHCl_3:MeOH$ (=20:1) mixed solvent) and then resolidified from $CHCl_3-Et_2O$ mixed solvent to give Boc-Gly-Pro-Leu-Gly-NHOH (0.70 g; 84%) as a colorless powder. m.p. 90°–104° C., specific rotation $[\alpha]_D^{28}$ −84.3 (c=1.0, EtOH).

TLC (developing solvent:① $CHCl_3:MeOH:AcOH=80:10:5$, ② $n-BuOH:AcOH:H_2O=4:1:1$; color developing method:(a) 0.1% ninhydrin spraying followed by heating, (b) 10% $Na_2CO_3$—and then 5% $FeCl_3$—spraying) gave single spots at Rf①=0.34 and Rf②=0.67.

EXAMPLE 2 t-ButyloxyCarbonyl-glyCyl-L-prolyl-L-leucyl-L-alanylhydroxamic acid (Boc-Gly-Pro-Leu-Ala-NHOH)

(A) Synthesis of Boc-Ala-NHOBzl

HCl·NHOBzl (2.07 g; 13.0 mmol) was dissolved in a mixed solvent of DMSO (10 ml) and DMF (30 ml), and TEA (2.0 ml; 14.3 mmol) was added dropwise under ice cooling. After the dropwise addition, HOBt (1.35 g; 10.0 mmol) and Boc-Ala-OH (1.89 g; 10.0 mmol) were added and the mixture was cooled with a coolant at −20° C. DCC (2.70 g; 13.1 mmol) dissolved in $CH_2Cl_2$ (10 ml) was added, and the reaction was carried out for 1 hour at −10° C. and overnight in a refrigerator. Insolubles were removed by filtration and the solvent was distilled off under reduced pressure. The residue was dissolved in AcOEt and washed successively with water, 1N-HCl, water, 10% $Na_2CO_3$ and water. The solution was dried over anhydrous $MgSO_4$ and the residue was purified by chromatography on silica gel (Fuji Davison BW 200, 170 g; eluted with AcOEt:n-hexane=2:3 mixed solvent) and then recrystallized from an AcOEt-n-hexane mixed solvent to give Boc-Ala-NHOBzl (2.68 g; 91%) as colorless needles. m.p. 98°–99° C., specific rotation $[\alpha]_D^{28}$ −42.1 (c=1.0, EtOH).

TLC (developing solvent:① $CHCl_3:MeOH=20:1$, ② $CHCl_3:MeOH:AcOH=95:5:3$; color developing method: 0.1% ninhydrin spraying followed by heating) gave single spots at Rf①=0.60 and Rf②=0.58.

(B) Synthesis Of Boc-Leu-Ala-NHOBzl

To Boc-Ala-NHOBzl (1.47 g; 4.99 mmol) obtained in (A) was added under ice cooling 4.5N-HCl/AcOEt (10 ml). After the mixture was brought back to room temperature, the reaction was carried out for 1 hour. The solvent was distilled off under reduced pressure and the residue was dissolved in THF (20 ml) and cooled with a coolant at −20° C. TEA (0.84 ml; 6.0 mmol) was added dropwise and HOBt (0.68 g; 5.03 mmol) and Boc-Leu-OH (product from azeotropic dehydration with benzene of the monohydrate (1.17 g; 4.69 mmol)) were added. DCC (1.35 g; 6.50 mmol) dissolved in THF (5 ml) was added dropwise, and the reaction was carried out for 1 hour at −10° C. and overnight in a refrigerator. Insolubles were removed by filtration and the solvent was distilled off under reduced pressure. The residue was dissolved in AcOEt and washed successively with water, 1N-HCl, water, 10% $Na_2CO_3$ and water. The solution was dried over anhydrous $MgSO_4$ and the solvent was distilled off under reduced pressure. The residue was solidified from AcOEt to give Boc-Leu-Ala-NHOBzl (1.53 g; 80%) as colorless crystals. m.p. 164°–166° C., specific rotation $[\alpha]_D^{28} -46.0$ (c=1.0, EtOH).

TLC (developing solvent: ① $CHCl_3$:MeOH=20:1, ② $CHCl_3$:MeOH:AcOH=95:5:3; color developing method: 0.1% ninhydrin spraying followed by heating) gave single spots at Rf①=0.52 and Rf②=0.60.

(C) Synthesis of Boc-Gly-Pro-Leu-Ala-NHOBzl

To Boc-Leu-Ala-NHOBzl (1.37 g; 3.36 mmol) obtained in (B) was added under ice cooling 4.5N-HCl/AcOEt (10 ml). After the mixture was brought back to room temperature the reaction was carried out for 2 hours. The solvent was distilled off under reduced pressure and the residue was dissolved in DMF (10 ml) and cooled with a coolant at −20° C. After TEA (0.49 ml; 3.50 mmol) was added dropwise, HOBt (0.43 g; 3.18 mmol) and Boc-Gly-Pro-OH (0.75 g; 3.05 mmol) obtained in Example 1 (E) were added. DCC (0.83 g; 4.00 mmol) dissolved in THF (5 ml) was added dropwise and the reaction was carried out for 1 hour at −10° C. and overnight in a refrigerator. Insolubles were removed by filtration and the solvent was distilled off under reduced pressure. The residue was dissolved in AcOEt and washed successively with water, 1N-HCl, water, 10% $Na_2CO_3$ and water. The solution was dried over anhydrous $MgSO_4$ and the solvent was distilled off under reduced pressure. The residue was purified by chromatography on silica gel (Fuji Davison BW 200, 100 g; eluted with $CHCl_3$:MeOH (=20:1) mixed solvent) and then recrystallized from an AcOEt-n-hexane mixed solvent to give Boc-Gly-Pro-Leu-Ala-NHOBzl (1.32 g; 81%) as colorless crystals. m.p. 103°–105° C., specific rotation $[\alpha]_D^{28} -72.1$ (c=1.0, EtOH).

TLC (developing solvent: ① $CHCl_3$:MeOH=14:1, ② $CHCl_3$:MeOH:AcOH=80:10:5; color developing method: 0.1% ninhydrin spraying followed by heating) gave single spots at Rf①=0.36 and Rf②=0.80.

(D) Synthesis of Boc-Gly-Pro-Leu-Ala-NHOH

Boc-Gly-Pro-Leu-Ala-NHOBzl (0.53 g; 0.94 mmol) obtained in (C) was dissolved in MeOH (10 ml) and the solution was subjected to catalytic hydrogenation at room temperature for 1 hour using 10% Pd-C (Engelhard 50% wet) (0.17 g). The catalyst was filtered off and the solvent was distilled off under reduced pressure. The residue was resolidified from a MeOH-$Et_2O$ mixed solvent to give Boc-Gly-Pro-Leu-Ala-NHOH (0.40 g; 86%) as a colorless powder. m.p. 112°–118° C., specific rotation $[\alpha]_D^{28} -85.0$ (c=1.0, EtOH).

TLC (developing solvent: ① $CHCl_3$:MeOH:AcOH=80:10:5, ② n-BuOH:AcOH:$H_2O$=4:1:1; color developing method:(a) 0.1% ninhydrin spraying followed by heating, (b) 10% $Na_2CO_3$ - and then 5% $FeCl_3$ - spraying) gave single spots at Rf①=0.39 and Rf②=0.67.

EXAMPLE 3 t-Butyloxycarbonyl-glycyl-L-prolyl-L-phenylalanyl-glycylhydroxamic acid
(Boc-Gly-Pro-Phe-Gly-NHOH)

(A) Synthesis of Boc-Phe-Gly-NHOBzl

HCl·Gly-NHOBzl (2.38 g; 11.0 mmol) obtained in Example 1 (B) was dissolved in a mixed solvent of DMF (6 ml) and THF (15 ml), and the solution was cooled with a coolant at −20° C. After TEA (1.54 ml; 11.0 mmol) was added dropwise, HOBt (1.42 g; 10.5 mmol) and Boc-Phe-OH (2.65 g; 10.0 mmol) were added and DCC (2.68 g; 13.0 mmol) dissolved in $CH_2Cl_2$ (10 ml) was added dropwise. The reaction was carried out for 1 hour at −10° C. and overnight in a refrigerator. Insolubles were filtered off and the solvent was distilled off under reduced pressure. The residue was dissolved in AcOEt and washed successively with water, 1N-HCl, water, 10% $Na_2CO_3$ and water. The solution was dried over anhydrous $MgSO_4$ and the solvent was distilled off under reduced pressure. The residue was purified by chromatography on silica gel (Fuji Davison BW 200, 100 g; eluted with $CHCl_3$:MeOH=50:1 mixed solvent) and solidified from benzene to give Boc-Phe-Gly-NHOBzl (3.75 g; 88%) as a colorless powder. m.p. 71°–72° C., specific rotation $[\alpha]_D^{28} +9.8$ (c=1.0, EtOH).

TLC (developing solvent: ① $CHCl_3$:MeOH=14:1, ② $CHCl_3$:MeOH:AcOH=95:5:3; color developing method: 0.1% ninhydrin spraying followed by heating) gave single spots at Rf①=0.75 and Rf②=0.62.

(B) Synthesis of Boc-Gly-Pro-Phe-Gly-NHOBzl

To Boc-Phe-Gly-NHOBzl (2.75 g; 6.44 mmol) obtained in (A) was added under ice cooling 4.5N-HCl/AcOEt (20 ml). The mixture was brought back to room temperature and the reaction was carried out for 1 hour. $Et_2O$ (30 ml) was added and insolubles precipitated thereby were then filtered off and dissolved in DMF (10 ml). The solution was cooled with a coolant at −20° C. and TEA (0.90 ml; 6.44 mmol) was added dropwise. HOBt (0.83 g; 6.14 mmol) and Boc-Gly-Pro-OH (1.59 g; 5.85 mmol) obtained in Example 1 (E) were then added and DCC (1.57 g; 7.61 mmol) dissolved in THF (5 ml) was added dropwise. The reaction was carried out for 1 hour at −10° C. and overnight in a refrigerator. Insolubles were removed by filtration and the solvent was distilled off under reduced pressure. The residue was dissolved in AcOEt and the solution was washed successively in water, 1N-HCl, water, 10% $Na_2CO_3$ and water. The solution was dried over anhydrous $MgSO_4$ and the solvent was distilled off under reduced pressure. The residue was solidified from a small volume of AcOEt to give Boc-Gly-Pro-Phe-Gly-NHOBzl (2.88 g; 85%) as a colorless powder. m.p. 87°–90° C., specific rotation $[\alpha]_D^{28} -71.8$ (c=1.0, EtOH).

TLC (developing solvent: ① $CHCl_3$:MeOH=14:1, ② $CHCl_3$:MeOH:AcOH=95:5:3; color developing method: 0.1% ninhydrin spraying followed by heating) gave single spots at Rf①=0.66 and Rf②=0.48.

(C) Synthesis of Boc-Gly-pro-Phe-Gly-NHOH

Boc-Gly-Pro-Phe-Gly-NHOBzl (0.80 g; 1.38 mmol) was dissolved in MeOH (10 ml) and the solution was subjected to catalytic hydrogenation at room temperature for 2 hours using 10% Pd-C (Engelhard, 50% wet; 0.14 g). The catalyst was removed by filtration and the solvent was distilled off under reduced pressure. The residue was solidified from a MeOH-Et$_2$O mixed solvent to give Boc-Gly-Pro-Phe-Gly-NHOH (0.46 g; 68%) as a colorless powder. m.p. 166°–171° C., specific rotation $[\alpha]_D^{28} - 89.7$ (c=1.0, MeOH).

TLC (developing solvent:① CHCl$_3$:MeOH:AcOH=80:10:5, ② n-BuOH:AcOH:H$_2$O=4:1:1; color developing method:(a) 0.1% ninhydrin spraying followed by heating, (b) 10% Na$_2$CO$_3$—and then 5% FeCl$_3$—spraying) gave single spots at R$_f$①=0.44 and R$_f$②=0.71.

EXAMPLE 4

Benzoyl-glycyl-L-prolyl-L-leucyl-glycyl-hydroxamic acid (Bz-Gly-Pro-Leu-Gly-NHOH)

(A) Synthesis of Bz-Gly-Pro-Leu-Gly-NHOBzl

To Boc-Gly-Pro-Leu-Gly-NHOBzl (0.55 g; 1.00 mmol) obtained in Example 1 (F) was added under ice cooling 4.5N HCl/AcOEt (2 ml), and the mixture was brought back to room temperature. The reaction was carried out for 1 hour. The solvent was distilled off under reduced pressure and the residue was dissolved in DMF (5 ml). The solution was cooled with a coolant at −20° C. and TEA (0.14 ml; 1.00 mmol) was added dropwise. Bz-Cl (0.17 g; 1.21 mmol) was then added dropwise and TEA was used to adjust the pH to 8–9. The reaction was carried out for 1 hour and insolubles were filtered off. The solvent was distilled off under reduced pressure. The residue was dissolved in AcOEt, and the solution was washed successively with water, 1N-HCl, water, 10% Na$_2$CO$_3$ and water and then dried over anhydrous MgSO$_4$. The solvent was distilled off under reduced pressure and the residue was purified by chromatography on silica gel (Fuji Davison BW 200, 25 g; eluted with CHCl$_3$:MeOH (=20:1) mixed solvent) to give Bz-Gly-Pro-Leu-Gly-NHOBzl (0.43 g; 78%) as a colorless powder. m.p. 79°–84° C., specific rotation $[\alpha]_D^{28} - 69.0$ (c=1.0, EtOH).

TLC (developing solvent:① CHCl$_3$:MeOH=14:1, ② CHCl$_3$:MeOH:AcOH=95:5:3; color developing method: 0.1% ninhydrin—and then 47% hydrobromic acid—spraying followed by heating) gave single spots at R$_f$①=0.22 and R$_f$②=0.65.

(B) Synthesis of Bz-Gly-Pro-Leu-Gly-NHOH

Bz-Gly-Pro-Leu-Gly-NHOBzl (0.30 g; 0.54 mmol) obtained in (A) was dissolved in MeOH (10 ml) and the solution was subjected to catalytic hydrogenation for 3.5 hours at room temperature using 5% Pd-C (Engelhard, 50% wet; 0.10 g). After the catalyst was filtered off, the solvent was distilled off under reduced pressure and the residue was recrystallized from an AcOEt-n-hexane mixed solvent to give Bz-Gly-Pro-Leu-Gly-NHOH (0.16 g; 65%) as a colorless powder. m.p. 118°–123° C., specific rotation $[\alpha]_D^{28} - 77.4$ (c=1.0, EtOH).

TLC (developing solvent:/ CHCl$_3$:MeOH:AcOH=80:10:5, ② n-BuOH:AcOH:H$_2$O=4:1:1; color developing method:(a) 0.1% ninhydrin spraying followed by heating, (b) 10% Na$_2$CO$_3$—and then 5% FeCl$_3$ spraying) gave single spots at R$_f$①=0.23 and R$_f$②=0.60.

EXAMPLE 5 t-Butyloxycarbonyl-glycyl-L-hydroxyprolyl-L-leucyl-glycylhydroxamic acid (Boc-Gly-Hyp-Leu-Gly-NHOH)

(A) Synthesis of Boc-Hyp-Leu-Gly-NHOBzl

To Boc-Leu-Gly-NHOBzl (3.89 g; 9.89 mmol) obtained in Example 1 (C) was added under ice cooling 4.5N-HCl/AcOEt (30 ml), and the solution was brought back to room temperature. The reaction was carried out for 1 hour. The solvent was distilled off under reduced pressure and the residue was dissolved in THF (100 ml). The solution was cooled with a coolant at −20° C. After TEA (1.40 ml; 10.0 mmol) was added dropwise, HOBt (1.22 g; 9.03 mmol) and Boc-Hyp-OH (1.99 g; 8.60 mmol) were added and DCC (2.31 g; 11.2 mmol) dissolved in THF (10 ml) was added dropwise. The reaction was carried out for 1 hour at −10° C. and overnight in a refrigerator. Insolubles were filtered off and the solvent was then distilled off under reduced pressure. The residue was dissolved in AcOEt and the solution was washed successively with water, 1N-HCl, water, 10% Na$_2$CO$_3$ and water and then dried over anhydrous MgSO$_4$. The solvent was distilled off under reduced pressure and the residue was recrystallized from AcOEt to give Boc-Hyp-Leu-Gly-NHOBzl (2.45 g; 56%) as colorless crystals. m.p. 168°–173° C., specific rotation $[\alpha]_D^{28} - 50.8$ (c=1.0, EtOH).

TLC (developing solvent:① CHCl$_3$:MeOH=14:1. ② CHCl$_3$:MeOH:AcOH=95:5:3; color developing method: 0.1% ninhydrin spraying followed by heating) gave single spots at R$_f$①=0.40 and R$_f$②=0.19.

(B) Synthesis of Boc-Gly-Hyp-Leu-Gly-NHOBzl

To Boc-Hyp-Leu-Gly-NHOBzl (2.00 g; 3.95 mmol) obtained in (A) was added under ice cooling 4.5N-HCl/AcOEt (10 ml) and the mixture was brought back to room temperature. The reaction was carried out for 1 hour. The precipitate was filtered off and dissolved in DMF (10 ml). TEA (0.55 ml; 3.95 mmol) was added dropwise under ice cooling, and Boc-Gly-ONSu (2.30 g; 7.87 mmol) was added. The mixture was brought back to room temperature and the reaction was carried out for 3 hours. Insolubles were filtered off and the solvent was distilled off under reduced pressure. The residue was dissolved in AcOEt and the solution was washed successively with water, 1N-HCl, water, 10% Na$_2$CO$_3$ and water and then dried over anhydrous MgSO$_4$. The solvent was distilled off under reduced pressure and the residue was purified by chromatography on silica gel (Fuji Davison BW 200, 100 g; eluted with CHCl$_3$:MeOH (=30:1) mixed solvent) to give Boc-Gly-Hyp-Leu-Gly-NHOBzl (1.57 g; 70%) as a colorless oil. Specific rotation $[\alpha]_D^{28} - 55.5$ (c=1.0, EtOH).

TLC (developing solvent:① CHCl$_3$:MeOH=14:1, ② n-BuOH:AcOH:H$_2$O=4:1:1; color developing method: 0.1% ninhydrin spraying followed by heating) gave single spots at R$_f$①=0.37 and R$_f$②=0.64.

(C) Synthesis of Boc-Gly-Hyp-Leu-Gly-NHOH

Boc-Gly-Hyp-Leu-Gly-NHOBzl (0.75 g; 1.33 mmol) obtained in (B) was dissolved in MeOH (10 ml) and the solution was subjected to catalytic hydrogenation for 1 hour at room temperature using 10% Pd-C (Engelhard, 50% wet; 0.25 g). The catalyst was filtered off and the solvent was distilled off under reduced pressure. The residue was resolidified from a MeOH-Et₂O mixed solvent to give Boc-Gly-Hyp-Leu-Gly-NHOH (0.5 g; 79%) as a colorless powder. m.p. 178°-183° C., specific rotation $[\alpha]_D^{28} -73.8$ (c=1.0, MeOH).

TLC (developing solvent:① CHCl₃:MeOH-:AcOH=5:2:1, ② n-BuOH:AcOH:H₂O=4:1:1; color developing method:(a) 0.1% ninhydrin spraying followed by heating, (b) 10% Na₂CO₃—and then 5% FeCl₃—spraying) gave single spots at R_f①=0.61 and R_f②=0.51.

EXAMPLE 6 p-Aminobenzyl-glycyl-L-prolyl-D-leucyl-D-alanyl-hydroxamic acid acetate
(AcOH.ABA-Gly-Pro-D-Leu-D-Ala-NHOH)

(A) Synthesis of Z-D-Leu-D-Ala-OMe

HCl·D-Ala-OMe (5.58 g; 40.0 mmol) was dissolved in DMF (100 ml) and TEA (5.6 ml; 40.0 mmol) was added dropwise under ice cooling. After HOSu (2.30 g; 20.0 mmol) and Z-D-Leu-OH (9.29 g; 35.0 mmol) were added, the mixture was cooled with a coolant at −20° C. and DCC (9.28 g; 45.0 mmol) dissolved in CH₂CL₂ (50 ml) was added dropwise. The reaction was carried out for 1 hour at −10° C. and overnight in a refrigerator. Insolubles were filtered off and the solvent was distilled off under reduced pressure. The residue was dissolved in AcOEt and the solution was washed successively with water, 1N-HCl, water, 10% Na₂CO₃ and water and dried over anhydrous MgSO₄. The solvent was distilled off under reduced pressure and the residue was solidified from an Et₂O-n-hexane mixed solvent to give Z-D-Leu-D-Ala-OMe (11.5 g; 94%) as a colorless powder. m.p. 94°-95° C., specific rotation $[\alpha]_D^{28}+35.9$ (c=1.0, EtOH).

TLC (developing solvent:① CHCl₃:MeOH=14:1, ② CHCl₃:MeOH:AcOH=95:5:3; color developing method: 0.1% ninhydrin - and then 47% hydrobromic acid spraying followed by heating) gave single spots at R_f①=0.82 and R_f②=0.78.

(B) Synthesis of Boc-Pro-D-Leu-D-Ala-OMe

Z-D-Leu-D-Ala-OMe (8.80 g; 25.1 mmol) obtained in (A) was dissolved in MeOH (80 ml) and 4.5N-HCl/AcOEt (10 ml) was added. The mixture was subjected to catalytic hydrogenation for 4 hours at room temperature using 10% Pd-C (Engelhard, 50% wet; 1.2 g). The catalyst was filtered off and the solvent was distilled off under reduced pressure. The residue was dissolved in THF (50 ml) and the solution was cooled with a coolant at −20° C. After TEA (3.50 ml; 25.0 mmol) was added dropwise, HOSu (1.73 g; 15.0 mmol) and Boc-Pro-OH (5.38 g; 25.0 mmol) were added and DCC (6.81 g; 33.0 mmol) dissolved in CH₂Cl₂ (30 ml) was added dropwise. The reaction was carried out for 1 hour at −10° C. and overnight in a refrigerator. Insolubles were filtered off and the solvent was distilled off under reduced pressure. The residue was dissolved in AcOEt and the solution was washed successively with water, 1N-HCl, water, 10% Na₂CO₃ and water and dried over anhydrous MgSO₄. The solvent was distilled off under reduced pressure and the residue was solidified from an Et₂O-n-hexane mixed solvent to give Boc-Pro-D-Leu-D-Ala-OMe (8.27 g; 85%) as a colorless powder. m.p. 153°-157° C., specific rotation $[\alpha]_D^{28}+11.6$ (c=1.0, EtOH).

TLC (developing solvent:① CHCl₃:MeOH=14:1, ② CHCl₃:MeOH:AcOH=95:5:3; color developing method: 0.1% ninhydrin spraying followed by heating) gave single spots at R_f①=0.80 and R_f②=0.63.

(C) Synthesis Of Z-Gly-Pro-D-Leu-D-Ala-OMe

To Boc-Pro-D-Leu-D-Ala-OMe (4.13 g; 10.0 mmol) obtained in (B) was added under ice cooling 4.5N-HCl/AcOEt (30 ml) and the mixture was brought back to room temperature and the reaction was carried out for 1.5 hours. The solvent was distilled off under reduced pressure and the residue was dissolved in DMF (30 ml). The solution was cooled with a coolant at −20° C. After TEA (1.40 ml; 10.0 mmol) was added dropwise, HOSu (0.58 g; 5.04 mmol) and Z-Gly-OH (2.10 g; 10.0 mmol) were added and DCC (2.60 g; 12.6 mmol) dissolved in CH₂Cl₂ (10 ml) was added dropwise. The reaction was carried out for 1 hour at −10° C. and overnight in a refrigerator. Insolubles were filtered off and the solvent was distilled off under reduced pressure. The residue was dissolved in AcOEt and the solution was washed successively with water, 1N-HCl, water, 10% Na₂CO₃ and water and dried over anhydrous MgSO₄. The solvent was distilled off under reduced pressure and the residue was recrystallized from an AcOEt-Et₂O mixed solvent to give Z-Gly-Pro-D-Leu-D-Ala-OMe (3.95 g; 78%) as colorless crystals. m.p. 130°-134° C., specific rotation $[\alpha]_D^{28}+11.8$ (c=1.0, EtOH).

TLC (developing solvent:① CHCl₃:MeOH=14:1, ② CHCl₃:MeOH:AcOH=95:5:3; color developing method: 0.1% ninhydrin - and then 47% hydrobromic acid spraying followed by heating) gave single spots at R_f①=0.74 and R_f②=0.58.

(D) Synthesis of Z-ABA-Gly-Pro-D-Leu-D-Ala-OMe

Z-Gly-Pro-D-Leu-D-Ala-OMe (2.00 g; 3.96 mmol) obtained in (C) was dissolved in MeOH (10 ml) and the solution was subjected to catalytic hydrogenation at room temperature for 2 hours using 10% Pd-C (Engelhard, 50% wet; 0.50 g). The catalyst was filtered off and the solvent was distilled off under reduced pressure. The residue was dissolved in DMF (15 ml) and the solution was cooled with a coolant at −20° C. HOBt (0.27 g; 2.00 mmol) and Z-ABA-OH (1.09 g; 4.02 mmol) were added in that order, and DCC (1.03 g; 4.99 mmol) dissolved in CH₂Cl₂ (5 ml) was added dropwise. The reaction was carried out for 1 hour at −10° C. and overnight in a refrigerator. Insolubles were filtered off and the solvent was distilled off under reduced pressure. The residue was dissolved in AcOEt and the solution was washed successively with water, 1N-HCl, water, 10% Na₂CO₃ and water and dried over anhydrous MgSO₄. The solvent was distilled off under reduced pressure and the residue was recrystallized from AcOEt to give Z-ABA-Gly-Pro-D-Leu-D-Ala-OMe (1.78 g; 72%) as a colorless powder. m.p. 109°-112° C., specific rotation $[\alpha]_D^{28}+4.7$ (c=1.0, EtOH).

TLC (developing solvent:① CHCl₃:MeOH=14:1, / CHCl₃:MeOH:AcOH=95:5:3; color developing method: 0.1% ninhydrin—and then 47% hydrobromic acid—spraying followed by heating) gave single spots at R_f①=0.65 and R_f②=0.46.

(E) Synthesis of Z-ABA-Gly-Pro-D-Leu-D-Ala-NHOH

To Z-ABA-Gly-Pro-D-Leu-D-Ala-OMe (1.68 g; 2.69 mmol) obtained in (D) was added under ice cooling a separately prepared 1M NH₂OH/MeOH solution [i.e. a solution obtained by adding dropwise under ice cooling NH₂OH.HCl (0.63 g; 9.06 mmol) dissolved in MeOH (4 ml) to a solution of KOH (1.00 g; 85%; 15.1 mmol) in MeOH (3 ml) and filtering off the precipitated KCl] (6 ml) and the reaction was carried out for 4 hours. 3N-HCl was used to adjust the pH to 2 and the precipitate was filtered off to give Z-ABA-Gly-Pro-D-Leu-D-Ala-NHOH (1.68 g; quantitative) as a colorless powder. m.p. 189°-191° C., specific rotation $[\alpha]_D^{28} + 10.4$ (c=1.0, EtOH).

TLC (developing solvent:① CHCl₃:MeOH=14:1, ② CHCl₃:MeOH:AcOH=95:5:3; color developing method: (a) 0.1% ninhydrin—and then 47% hydrobromic acid spraying followed by heating, (b) 10% Na₂CO₃—and then 5% FeCl₃ spraying) gave single spots at R$_f$①=0.40 and R$_f$②=0.14.

(F) Synthesis of AcOH.ABA-Gly-Pro-D-Leu-D-Ala-NHOH

Z-ABA-Gly-Pro-D-Leu-D-Ala-NHOH (1.40 g; 2.24 mmol) obtained in (E) was dissolved in an AcOH:water (=2:1) mixed solvent (10 ml) and the solution was subjected to catalytic hydrogenation at room temperature for 2.5 hours using 10% Pd-C (Engelhard, 50% wet; 0.35 g). The catalyst was distilled off and the solvent was distilled off under reduced pressure. The residue was recrystallized from EtOH to give AcOH.ABA-Gly-Pro-D-Leu-D-Ala-NHOH (0.93 g; 75%) as a colorless powder. m.p. 213°-218° C., specific rotation $[\alpha]_D^{28} + 23.4$ (c=0.5, H₂O).

TLC (developing solvent:① CHCl₃:MeOH:AcOH=80:0:5, ② n-BuOH:AcOH:H₂O=4:1:1; color developing method:(a) 0.1% ninhydrin spraying followed by heating, (b) 10% Na₂CO₃—and then 5% FeCl₃—spraying) gave single spots at R$_f$①=0.25 and R$_f$②=0.58.

EXAMPLE 7 p-Hydroxybenzoyl-glycyl-L-prolyl-D-leucyl-D-alanyl-hydroxamic acid
(HBA-Gly-Pro-D-Leu-D-Ala-NHOH)

(A) Synthesis of Bzl-HBA-Gly-Pro-D-Leu-D-Ala-OMe

Z-Gly-Pro-D-Leu-D-Ala-OMe (1.73 g; 3.43 mmol) obtained in Example 6 (C) was dissolved in MeOH (5 ml) and the solution was subjected to catalytic hydrogenation at room temperature for 2 hours using 10% Pd-C (Engelhard, 50% wet; 0.30 g). The catalyst was filtered off and the solvent was distilled off under reduced pressure. The residue was dissolved in DMF (10 ml) and cooled with a coolant at −20° C. Bzl-HBA-Cl [prepared by dissolving Bzl-HBA-OH (1.17 g; 5.15 mmol) in SOCl₂ (5 ml), heating the solution under reflux for 3 hours and distilling off the excess SOCl₂ under reduced pressure] dissolved in DMF (3 ml) was added dropwise. TEA was used to adjust the pH to 8 and the reaction was carried out for 4 hours. Insolubles were filtered off and the solvent was distilled off under reduced pressure. The residue was dissolved in AcOEt and the solution was washed successively with water, 1N-HCl, water, 10% Na₂CO₃ and water and dried over anhydrous MgSO₄. The solvent was distilled off under reduced pressure and the residue was subjected to chromatography on silica gel (Fuji Davison BW 200, 15 g; eluted with AcOEt) to give Bzl-HBA-Gly-Pro-D-Leu-D-Ala-OMe (1.23 g; 62%) as a colorless oil. Specific rotation $[\alpha]_D^{28} + 4.6$ (c=1.0, EtOH).

TLC (developing solvent:① CHCl₃:MeOH=14:1, ② CHCl₃:MeOH:AcOH=95:5:3; color developing method: 0.1% ninhydrin—and then 47% hydrobromic acid—spraying followed by heating) gave single spots at R$_f$①=0.73 and R$_f$②=0.58.

(B) Synthesis of Bzl-HBA-Gly-Pro-D-Leu-D-Ala-NHOH

To Bzl-HBA-Gly-Pro-D-Leu-D-Ala-OMe (1.15 g; 1.98 mmol) obtained in (A) was added under ice cooling 1M-NH2OH/MeOH (5 ml) prepared in the same manner as in Example 6 (E) and the reaction was carried out for 3 hours. 3N-HCl was used to adjust the pH to 2 and the precipitate was filtered off and resolidified from a MeOH-Et₂O mixed solvent to give Bzl-HBA-Gly-Pro-D-Leu-D-Ala-NHOH (0.87 g; 76%) as a colorless powder. m.p. 181°-184° C., specific rotation $[\alpha]_D^{28} + 13.6$ (c=1.0, EtOH).

TLC (developing solvent:① CHCl₃:MeOH=14:1, ② CHCl₃:MeOH:AcOH=95:5:3; color developing method: (a) 0.1% ninhydrin—and then 47% hydrobromic acid—spraying followed by heating, (b) 10% Na₂CO₃—and then 5% FeCl₃- spraying) gave single spots at R$_f$①=0.51 and R$_f$②=0.25.

(C) Synthesis of HBA-Gly-Pro-D-Leu-D-Ala-NHOH

Bzl-HBA-Gly-Pro-D-Leu-D-Ala-NHOH (0.83 g; 1.43 mmol) obtained in (B) was dissolved in MeOH (5 ml) and the solution was subjected to catalytic hydrogenation at room temperature for 2 hours using 10% Pd-C (Engelhard, 50% wet; 0.15 g). The catalyst was filtered off and the solvent was distilled off under reduced pressure. The residue was solidified from a MeOH-Et₂O mixed solvent to give HBA-Gly-Pro-D-Leu D Ala-NHOH (0.53 g; 76%) as a colorless powder. m.p. 159°-164° C., specific rotation $[\alpha]_D^{28} + 12.6$ (c=0.5, EtOH).

TLC (developing solvent:① CHCl₃:MeOH:AcOH=80:10:5, ② n-BuOH:AcOH:water=4:1:1; color developing method:(a) 0.1% ninhydrin—and then 47% hydrobromic acid spraying followed by heating, (b) 10% Na₂CO₃—and then 5% FeCl₃—spraying) gave single spots at R$_f$①=0.27 and R$_f$②=0.67.

EXAMPLES 8-42

In accordance with the procedure as described in Examples 1-7, the compounds indicated in Table 1 were prepared. Data for the compounds obtained in the respective Examples are as shown in Table 1.

TABLE 1

| Example No. | Compound (as indicated by formula) | m.p. °C. | $[\alpha]_D^{28}$ | TLC:R$_f$[1] | Process for synthesis |
|---|---|---|---|---|---|
| 8 | HCl.Gly—Pro—Leu—Gly—NHOH | hygroscopic | −87.2(c = 0.5, EtOH) | ③0.24 | A |
| 9 | HCl.Sar—Pro—Leu—Gly—NHOH | hygroscopic | −79.1(c = 1.0, EtOH) | ②0.19 | A |
| 10 | Ac—Gly—Pro—Leu—Gly—NHOH | 109~115 | −91.3(c = 1.0, EtOH) | ①0.13②0.43 | A |
| 11 | HCl Bzl—Gly—Pro—Leu—Gly—NHOH | hygroscopic | −72.6(c = 0.5, EtOH) | ①0.09②0.45 | A |

TABLE 1-continued

| Example No. | Compound (as indicated by formula) | m.p. °C. | $[\alpha]_D^{28}$ | TLC:$R_f$[1] | Process for synthesis |
|---|---|---|---|---|---|
| 12 | Boc—Sar—Pro—Leu—Gly—NHOH | 94~99 | −80.6(c = 1.0, EtOH) | ①0.42②0.66 | A |
| 13 | Ac—Sar—Pro—Leu—Gly—NHOH | hygroscopic | −88.2(c = 0.5, EtOH) | ①0.15②0.37 | A |
| 14 | Boc\<br>    Gly—Pro—Leu—Gly—NHOH<br>Bzl/ | hygroscopic | −73.8(c = 0.5, EtOH) | ①0.54②0.71 | A |
| 15 | Boc—Gly—Pro—Leu-β-Ala—NHOH | 108~112 | −70.2(c = 1.0, EtOH) | ①0.38②0.64 | A |
| 16 | Boc—Gly—Pro—Leu—GAB—NHOH | 88~93 | −56.9(c = 1.0, EtOH) | ①0.38②0.64 | A |
| 17 | Boc—Gly—Pro—Leu-D-Ala—NHOH | 115~120 | −89.3(c = 1.0, EtOH) | ①0.55②0.70 | A |
| 18 | Boc—Gly—Pro—Leu—Val—NHOH | 118~123 | −113.6(c = 1.0, EtOH) | ①0.53②0.73 | A |
| 19 | HCl.Gly—Pro—Leu-β-Ala—NHOH | hygroscopic | −21.8(c = 1.0, EtOH) | ③0.27 | A |
| 20 | HCl.Gly—Pro—Leu—GAB—NHOH | hygroscopic | −51.5(c = 1.0, EtOH) | ③0.22 | A |
| 21 | Boc—Gly—Pro-D-Leu—Gly—NHOH | 96~100 | −20.3(c = 1.0, EtOH) | ①0.50②0.73 | A |
| 22 | Boc—Gly—Pro—Gln—Gly—NHOH | hygroscopic | −67.1(c = 1.0, EtOH) | ①0.08②0.43 | A |
| 23 | Boc—Gly—Pro—Glu—Gly—NHOH | 94~100 | −64.9(c = 1.0, EtOH) | ①0.12②0.49 | A |
| 24 | Boc—Gly—Pro—Gly—Gly—NHOH | 178~180 | −52.3(c = 1.0, DMF) | ①0.16②0.44 | A |
| 25 | Boc—Gly—Pro—Ile—Gly—NHOH | 126~129 | −78.3(c = 1.0, EtOH) | ①0.37②0.64 | A |
| 26 | Boc—Gly—Pro—Ser—Gly—NHOH | 101~105 | −72.1(c = 1.0, EtOH) | ①0.12②0.45 | A |
| 27 | Boc—Gly—Pro—Lys—Gly—NHOH | hygroscopic | −56.5(c = 1.0, EtOH) | ②0.25 | A |
| 28 | Boc—Gly—Pro—Pro—Gly—NHOH | hygroscopic | −98.1(c = 1.0, EtOH) | ①0.31②0.46 | A |
| 29 | HCl<br>  \<br>HCl.Gly—Pro—Arg—Gly—NHOH | hygroscopic | −65.2(c = 1.0, H₂O) | ④0.16 | A |
| 30 | Boc—Gly—Gly—Leu—Gly—NHOH | 126~129 | −12.5(c = 1.0, EtOH) | ①0.18②0.65 | A |
| 31 | Boc—Gly—Ala—Leu—Gly—NHOH | 149~152 | −42.2(c = 1.0, EtOH) | ①0.24②0.67 | A |
| 32 | Bz—Gly-D-Pro—Leu—Gly—NHOH | 99~105 | +18.4(c = 1.0, EtOH) | ①0.55②0.70 | A |
| 33 | Bz—Gly-thioPro—Leu—Gly—NHOH | 166~169 | −96.8(c = 0.5, MeOH) | ①0.30②0.67 | A |
| 34 | Bz—Gly—Pro—Leu—Ala—NHOH | 202~204 | −71.7(c = 1.0, DMF) | ①0.78②0.75 | A |
| 35 | Bz—Gly—Pro-D-Leu-D-Ala—NHOH | 172~174 | +10.8(c = 1.0, DMF) | ①0.63②0.70 | A |
| 36 | Bz—Gly—Pro—Leu—Sar—NHOH | 107~110 | −94.5(c = 1.0, EtOH) | ①0.44②0.58 | A |
| 37 | Bz—Gly—Pro-D-L-Sar—NHOH | 116~119 | −36.9(c = 1.0, DMF) | ①0.49②0.60 | A |
| 38 | Bz—Gly—Pro—Leu—Leu—NHOH | 131~135 | −74.0(c = 0.5, EtOH) | ①0.35②0.66 | A |
| 39 | Bz—Gly—Pro-D-Leu-D-Leu—NHOH | 187~190 | +25.6(c = 0.5, EtOH) | ①0.69②0.74 | A |
| 40 | PTH—Gly—Pro-D-Leu-D-Leu—NHOH | 159~164 | +17.8(c = 0.5, EtOH) | ①0.15②0.51 | A |
| 41 | AcOH.ABA—Gly—Pro—Leu—Ala—NHOH | 229~232 | −116(c = 1.0, AcOH:H₂O = 3:2) | ①0.08②0.45 | B |
| 42 | Bz—Gly—Pro—Leu-D-Ala—NHOH | 119~123 | −98.1(c = 1.0, DMF) | ①0.49②0.66 | A |

[1] developing solvent:
① CHCl₃:MeOH:AcOH = 80:10:5
② n-BuOH:AcOH:H₂O = 4:1:1
③ n-BuOH:AcOH:H₂O = 4:2:1
④ n-BuOH:AcOH:H₂O = 4:3:3
Color developing method:
(a) 0.1% ninhydrin - and then 47% hydrobromic acid spraying followed by heating.
(b) 10% Na₂CO₃ - and then 5% FeCl₃-spraying Using the following procedures, the new peptide compounds of the invention were assayed for inhibitory activity against collagenases as well as against other enzymes:

(1) Inhibitory activity against collagenases

The inhibitory activity against human fibroblast collagenase (collagenase derived from human fibroblasts), tadpole-derived collagenase and bacteria (Clostridium)-derived collagenase was assayed in accordance with the method of Nagai [see Ensho, 4(2), 123 (1984)] using a fluorescence-labeled collagen (FITC-derivatized bovine type I collagen).

(2) Inhibitory activity against urease

The inhibitory activity against urease was assayed in accordance with the method of Kobashi et al. [see Biochem. Biophys. Acta, 227 429 (1971)] using sword bean-derived urease.

(3) Inhibitory activity against thermolysin, trypsin and α-chymotrypsin

This was assayed in accordance with the method of Laskowski [see Meth. Enzymol., 2, 8 (1955)] using a thermally denatured casein as substrate for the respective enzymes (i.e. thermolysin, trypsin and α-chymotrypsin).

Results of these assays are shown in Table 2.

TABLE 2

| | IC$_{50}$ (μM) | | Inhibition (%) | | | | |
|---|---|---|---|---|---|---|---|
| Example No. | Human fibroblast collagenase | Tadpole collagenase | Bacterial collagenase | Urease | Thermolysin | Trypsin | α-Chymotrypsin |
| 6 | 1.28 | 1.10 | 7.1%/<br>2.0 × 10⁻⁴ M | 2.0%/<br>4.0 × 10⁻³ M | 26.8%/<br>4.0 × 10⁻³ M | 6.5%/<br>2.0 × 10⁻³ M | 26.4%/<br>2.0 × 10⁻³ M |
| 7 | 1.18 | 1.05 | 20.9%/<br>4.0 × 10⁻³ M | 5.3%/<br>4.0 × 10⁻³ M | 60.4%/<br>4.0 × 10⁻³ M | 56.1%/<br>4.0 × 10⁻³ M | 22.3%/<br>4.0 × 10⁻³ M |

TABLE 2-continued

| Example No. | IC50 (μM) Human fibroblast collagenase | Tadpole collagenase | Inhibition (%) Bacterial collagenase | Urease | Thermolysin | Trypsin | α-Chymotrypsin |
|---|---|---|---|---|---|---|---|
| 18 | 3.1 | 9.8 | 50.0%/ 3.4 × 10⁻² M | 22.0%/ 2.0 × 10⁻² M | 50.0%/ 1.01 × 10⁻² M | 0%/ 4.0 × 10⁻³ M | 0%/ 4.0 × 10⁻³ M |
| 34 | 2.7 | 7.7 | 34.0%/ 1.2 × 10⁻³ M | 0%/ 4.0 × 10⁻³ M | 35.0%/ 4.0 × 10⁻³ M | 0%/ 2.0 × 10⁻⁴ M | 0%/ 2.0 × 10⁻⁴ M |
| 35 | 6.4 | 3.1 | 33.0%/ 3.0 × 10⁻³ M | 24.0%/ 3.0 × 10⁻³ M | 38.0%/ 4.0 × 10⁻³ M | 2.2%/ 1.0 × 10⁻⁴ M | 12.8%/ 1.0 × 10⁻⁴ M |
| 40 | 3.6 | 3.1 | 20.7%/ 4.0 × 10⁻³ M | 3.3%/ 4.0 × 10⁻³ M | 32.2%/ 4.0 × 10⁻³ M | 21.6%/ 1.0 × 10⁻² M | 22.3%/ 1.0 × 10⁻² M |
| 41 | 3.7 | 4.0 | 0%/ 5.0 × 10⁻⁵ M | 3.3%/ 3.4 × 10⁻⁵ M | 4.0%/ 2.0 × 10⁻⁵ M | 14.4%/ 2.0 × 10⁻⁵ M | 27.3%/ 2.0 × 10⁻⁵ M |

The new peptides of the invention are extremely useful since they are found to have a specific inhibitory activity against collagenase as compared to known peptide substances.

The toxicity of the new peptide compounds of this invention is as follows:

Acute toxicity test (LD50) in mice

| Compound (as indicated by Example No.) | LD50 Intraperitoneal administration | Intravenous administration |
|---|---|---|
| 6 | >2 g/kg | >200 mg/kg |
| 7 | >2 g/kg | >200 mg/kg |
| 41 | >2 g/kg | >200 mg/kg |

We claim:

1. A peptidylhydroxamic acid derivative of the general formula:

$$X^1\text{-}X^2\text{-}X^3\text{-}X^4\text{-NHOH} \qquad (I)$$

wherein $X^1$ is a residue of an α-amino acid selected from glycine and sarcosine, $X^2$ is a residue of an amino acid selected from proline, hydroxyproline, thioproline and alaine, $X^3$ is a residue of an amino acid selected from glutamine, glutamic acid, leucine, isoleucine and phenylalanine and $X^4$ is a residue of an α-amino acid selected from glycine, alanine, valine, leucine and sarcosine; and the carboxyl group of α-amino acide $X^1$ forms a peptide bond together with the amino group of α-amino acid $X^2$, the carboxyl group of α-amino acid and acid $X^2$ forms a peptide bond together with the amino group of α-amino acid $X^3$, the caboxyl group of α-amino acid $X^3$ forms a peptide bond together with the amino group of α-amino acid $X^4$ and the carboxyl group of α- amino acid $X^4$ forms an amido together with —NHOH; and the hydrogen atom of the amino group in said α-amino acids $X^1$ may be replaced with a member selected from the group consisting of acetyl, benzoyl, benzyloxy, t-butyloxycarbonyl, benzyloxycarbonyl, p-aminobenzoyl, p-amino-benzyl, p-hydroxybenzoyl or a pharmaceutically acceptable salt thereof.

2. The peptidylhydroxamic acid derivative according to claim 1, wherein $X^1$ is glycine; $X^2$ is proline; $X^3$ is leucine; and $X^4$ is glycine.

3. A peptidylhydroxamic acid derivative according to claim 1, of the general formula:

$$X^1\text{-}X^2\text{-}X^3\text{-}X^4\text{-NHOH}$$

wherein $X^1$ is glycine;
$X^2$ is proline;
$X^4$ is alanine or leucine; and
wherein a hydrogen atom of the amino group of $X^1$ may be replaced with a member selected from the group consisting of acetyl, benzoyl, benzyloxy, t-butyloxycarbonyl, benzyloxycarbonyl, p-aminobenzoyl, p-aminobenzyl, p-hydroxybenzoyl; or a pharmaceutically acceptable salt thereof.

4. A method of inhibiting collagenases which comprises administering to a patient in need thereof a collagenase inhibiting effective amount of the compound according to claim 1.

5. A method of inhibiting collagenases which comprises administering to a patient in need thereof a collagenase inhibiting effective amount of the compound according to claim 3.

6. The peptidylhydroxamic acid derivative according to claim 3, which has the formula:
p-aminobenzoyl-Gly-Pro-D-Leu-D-Ala-NHOH, or a pharmaceutically acceptable salt thereof.

7. The peptidylhydroxamic acid derivative according to claim 3, which has the formula:
p-hydroxybenzoyl-Gly-Pro-D-Leu-D-Ala-NHOH, or a pharmaceutically acceptable salt thereof.

8. The peptidylhydroxamic acid derivative according to claim 2, wherein $X^3$ is D-Leu.

9. The peptidylhydroxamic acid derivative according to claim 3, wherien $D^3$ is D-Leu and $X^4$ is D-Ala.

10. The peptidylhydroxamic acid derivative according to claim 3, wherein $X^3$ is D-Leu and $X^4$ is D-Leu.

* * * * *